United States Patent [19]
Furcht et al.

[11] Patent Number: 5,591,719
[45] Date of Patent: Jan. 7, 1997

[54] METHOD FOR TREATING ACUTE AND CHRONIC INFLAMMATORY DISORDERS USING POLYPEPTIDES WITH FIBRONECTIN ACTIVITY

[75] Inventors: Leo T. Furcht; James B. McCarthy, both of Minneapolis, Minn.; Sharon M. Wahl, Gaithersburg; Janice B. Allen, Wheaton, both of Md.

[73] Assignees: Regents of the University of Minnesota, Minneapolis, Minn.; The United States of America as represented by the Secretary of Health and Human Services, Washington, D.C.

[21] Appl. No.: 990,296

[22] Filed: Dec. 10, 1992

[51] Int. Cl.$^6$ .............................. A61K 38/00; C07K 7/06; C07K 7/10

[52] U.S. Cl. ................. 514/13; 514/12; 514/14; 514/15; 514/16; 530/326; 530/329; 530/328; 530/324

[58] Field of Search ................ 514/12, 13, 14, 514/15, 16

[56] References Cited

U.S. PATENT DOCUMENTS

| | | | |
|---|---|---|---|
| 3,966,902 | 6/1976 | Chromecek | 424/59 |
| 4,440,860 | 4/1984 | Klagsbrun | 435/240 |
| 4,517,686 | 5/1985 | Ruoslahti et al. | 623/11 |
| 4,578,079 | 3/1986 | Ruoslahti et al. | 623/11 |
| 4,804,745 | 2/1989 | Koepff et al. | 424/59 |
| 4,839,464 | 6/1989 | McCarthy et al. | 530/326 |
| 4,870,160 | 9/1989 | Charonis et al. | 530/326 |
| 4,876,332 | 10/1989 | Tsilibary et al. | 530/326 |
| 5,019,646 | 5/1991 | Furcht et al. | 530/326 |
| 5,081,031 | 1/1992 | Tsilibary et al. | 435/240.23 |
| 5,082,926 | 1/1992 | Chelberg et al. | 530/326 |
| 5,116,368 | 5/1992 | McCarthy et al. | 623/2 |
| 5,152,784 | 10/1992 | Tsilibary | 623/1 |
| 5,171,271 | 12/1992 | Furcht et al. | 623/11 |

FOREIGN PATENT DOCUMENTS

| | | | |
|---|---|---|---|
| WO84/00540 | 2/1984 | WIPO | A61F 02/06 |
| WO88/03810 | 6/1988 | WIPO | A61F 02/02 |
| WO91/15236 | 1/1991 | WIPO | A61F 02/06 |
| WO92/00995 | 1/1992 | WIPO | A61F 02/16 |

OTHER PUBLICATIONS

S. M. Albelda et al., *FASEB J.*, 4, 2868–2880 (1990).
J. B. Allen et al., *Cytokine*, 3, 98–106 (1991).
J. B. Allen et al., *J. Clin. Invest.*, 76, 1042–1056 (1985).
M. Aumailley et al., *J. Cell. Biol.*, 103, 1569–1576 (1986).
W. Babel et al., *Eur. J. Biochem.*, 143, 545–556 (1984).
M. E. Brandes et al., *J. Clin. Invest.*, 87, 1108–1113 (1991).
D. Brazel et al., *Eur. J. Biochem.*, 168, 529–536 (1987).
D. Brazel et al., *Eur. J. Biochem.*, 172, 35–42 (1988).
J. M. Brinker et al., *Proc. Natl. Acad. Sci. USA*, 82, 3649–3653 (1985).
M. K. Chelberg et al., *Cancer Research*, 49, 4796–4802 (1989).
Z. Dische et al., *J. Biol. Chem.*, 175, 595–603 (1948).
L. Furcht et al., *Biochem. and Molec. Genetics of Cancer Metastasis*, K. Lapis et al., eds. (1985) at pp. 43–53.
L. T. Furcht, *Modern Cell Biology*, vol. 1, B. Satir, ed., Alan R. Liss, Inc., New York (1983) at pp. 53–117.
A. Garcia–Pardo et al., *Biochem. J.*, 241, 923–928 (1987).
A. Garcia–Pardo et al., *Immunology*, 69, 121–126 (1990).
R. W. Glanville et al., *Eur. J. Biochem.*, 152, 213–219 (1985).
T. J. Herbst et al., *J. Cell Biol.*, 106, 1365–1373 (1988).
R. M. Hewick et al., *J. Biol. Chem.*, 256, 7990–7997 (1981).
M. J. Humphries et al., *J. Biol. Chem.*, 262, 6886–6892 (1987).
H. E. Kambic et al., *Chem. and Eng. News*, pp. 30–48 (Apr. 14, 1986).
G. G. Koliakos et al., *J. Biol. Chem.*, 264, 2313–2323 (1989).
A. R. Kornblihtt et al., *EMBO J.*, 4, 1755–1759 (1985).
M. Kurkinen et al., *J. Biol. Chem.*, 259, 5915–5922 (1984).
J. Kyte et al., *J. Mol. Biol.*, 157, 105–132 (1982).
A. Laffon et al., *J. Clin. Invest.*, 88, 546–552 (1991).
S. M. Louis et al., *Neuroscience*, 39, 727–731 (1990).
J. B. McCarthy et al., *Biochemistry*, 27, 1380–1388 (1988).
J. B. McCarthy et al., *J. Cell. Biol.*, 102, 179–188 (1986).
J. B. McCarthy et al., *J. Natl. Cancer Inst.*, 80, 108–116 (1988).
J. C. Murray et al., *J. Cell. Biol.*, 80, 197–202 (1979).
G. Muthukumaran et al., *J. Biol. Chem.*, 264, 6310–6317 (1989).
I. Oberbaumer et al., *Eur. J. Biochem.*, 147, 217–224 (1985).
H. Pande et al., *Eur. J. Biochem.*, 162, 403–411 (1987).
T. E. Petersen et al., *Proc. Natl. Acad. Sci. USA*, 80, 137–141 (1983).
M. D. Pierschbacher et al., *Proc. Natl. Acad. Sci. USA*, 81, 5985–5988 (1984).
M. D. Pierschbacher et al., *Nature*, 309, 30–33 (1984).
T. Pihlajaniemi et al., *J. Biol. Chem.*, 260, 7681–7687 (1985).
S. L. Rogers et al., *Devel. Biol.*, 98, 212–220 (1983).
E. Ruoslahti, *J. Clin. Invest.*, 87, 1–5 (1991).
J. Saus et al., *J. Biol. Chem.*, 264, 6318–6324 (1989).
S. M. Schwartz, *In Vitro*, 14, 966–980 (1978).
U. Schwarz–Magdolen et al., *FEBS Lett.*, 208, 203–207 (1986).

(List continued on next page.)

*Primary Examiner*—Elizabeth C. Weimar
*Assistant Examiner*—S. G. Marshall
*Attorney, Agent, or Firm*—Merchant & Gould, Smith, Edell, Welter & Schmidt

[57] ABSTRACT

A method for treating acute or chronic inflammatory or autoimmune disorders using polypeptides with fibronectin or related activity is provided. The method involves (administering an amount of) one or more polypeptides corresponding to isolated amino acid residue sequences of the 33 kD carboxy terminal heparin-binding region located on the A chain of fibronectin to effectively suppress inflammation and impairment of tissue function in a patient.

17 Claims, 3 Drawing Sheets

OTHER PUBLICATIONS

J. E. Schwarzbauer et al., *Cell*, 35, 421–431 (1983).

D. M. Shotten et al., *J. Mol. Biol.*, 131, 303–329 (1979).

D. E. Smith et al., *J. Biol. Chem.*, 257, 6518–6523 (1982).

R. Soininen et al., *FEBS Lett.*, 225, 188–194 (1987).

T. A. Springer, *Nature*, 346, 425–434 (1990).

S. P. Sugrue, *J. Biol. Chem.*, 262, 3338–3343 (1987).

R. Timpl et al., *New Trends in Basement Membrane Research*, K. Kuehn et al., eds., Raven Press, NY (1982) at pp. 57–67.

K. J. Tomaselli et al., *J. Cell. Biol.*, 105, 2347–2358 (1987).

E. C. Tsilibary et al., *J. Cell. Biol.*, 103, 2467–2473 (1986).

E. C. Tsilibary et al., *J. Biol. Chem.*, 263, 19112–19118 (1988).

S. M. Wahl et al., *J. Exp. Med.*, 168, 1403–1417 (1988).

X–d. Yang et al., *J. Autoimmun.*, 3, 11–23 (Feb. 1990).

METHOD FOR TREATING ACUTE AND CHRONIC INFLAMMATORY DISORDERS USING POLYPEPTIDES WITH FIBRONECTIN ACTIVITY

BACKGROUND OF THE INVENTION

The adhesion of mammalian cells to the extracellular matrix is of fundamental importance in regulating growth, adhesion, motility and the development of proper cellular phenotype. This has implications for normal development, wound healing, immunity, chronic inflammatory diseases, and tumor metastasis. Evidence accumulated over the last several years suggests that the molecular basis for the adhesion of both normal and transformed cells is complex and probably involves several distinct cell surface molecules. Extracellular matrices consist of three types of macromolecules: collagens, proteoglycans and noncollagenous glycoproteins. The extracellular matrix molecule which has been most intensively studied with regard to cell adhesion is the noncollagenous cell adhesion glycoprotein, fibronectin, which is present in plasma, cell matrices, basal lamina and on cell surfaces. The fibronectin from plasma consists of a disulfide-bonded dimer having a molecular weight of 450,000 daltons. The two subunit chains ("A" and "B"), each of about 220,000 daltons, are observed under reducing conditions. This form of fibronectin will be referred to as "fibronectin" hereinafter.

Polypeptides from a 33 kD carboxyl terminal heparin-binding fragment of the A subunit fibronectin which promote adhesion and spreading of endothelial cells and melanoma cells are described in U.S. Pat. Nos. 4,839,464 and 5,019,646. The synthetic polypeptides corresponding to fibronectin residues described in these patents are disclosed as useful to (a) assist in nerve regeneration, (b) promote wound healing and implant acceptance, (c) promote cellular attachment to culture substrata, and (d) inhibit metastasis of malignant cells.

Evolution of inflammatory and immune reactions is dependent upon the recruitment and migration of circulating leukocytes to sites of injury or antigen deposition. The accumulation of leukocytes is dependent not only on chemotactic signals emanating from the inflammatory site, but also on cell-cell and cell-matrix interactions. Many of these cellular and matrix interactions are dependent upon expression of cell surface adhesion molecules (CAMs) [integrins, cell surface proteoglycans, selectins, etc.] which facilitate targeting and retention of circulating cells to sites of immunologic challenge [T. Springer, *Nature*, 346: 425–434 (1990); S. M. Albeda et al., *FASEB J.*, 4: 2668–2680 (1990); Ruoslahti, *J. Clin. Invest.*, 87: 1–5 (1991)].

Integrins represent a family of cell surface αβ heterodimeric proteins that mediate cell adhesion to other cells and to extracellular matrix constituents, including fibronectin. Although the role of integrins and other CAMs in mediating arrest and adhesion of inflammatory cells prior to extravasation is complex and poorly understood, emerging evidence suggests that integrins may be pivotal in these events. Therefore, a need exists for a method employing an agent that inhibits or modulates emigration of circulating cells to the site of immunologic challenge as a mechanism to regulate inflammation and its associated disorders.

SUMMARY OF THE INVENTION

The present invention provides a method for treating a number of disease states such as, for example, conditions associated with inflammatory disorders by administering to the patient an effective amount of compositions containing a polypeptide having a sequence of four or more amino acids corresponding substantially to an amino acid sequence within the 33 kD carboxyl terminal heparin-binding region located on the A chain of fibronectin. Preferably, the method involves administering an effective amount of a polypeptide or mixture of polypeptides having the formula:

tyr-glu-lys-pro-gly-ser-pro-pro-arg-glu-val-val-pro-arg-pro-arg-pro-gly-val (I) [sequence No. 1], lys-asn-asn-gln-lys-ser-glu-pro-leu-ile-gly-arg-lys-lys-thr (II) [sequence No. 2], trp-gln-pro-pro-arg-ala-arg-ile (V) [sequence No. 3], asp-glu-leu-pro-gln-leu-val-thr-leu-pro-his-pro-asn-leu-his-gly-pro-glu-ile-leu-asp-val-pro-ser-thr (CS-1) [sequence No. 4], and ser-pro-pro-arg-arg-ala-arg-val-thr (IV) [sequence No. 5].

Polypeptide I formula represents isolated fibronectin residues 1906–1924. Polypeptide II represents isolated fibronectin residues 1946–1960. Polypeptide IV represents isolated fibronectin residues 1784–1792. Polypeptide V represents isolated fibronectin residues 1892–1899. Polypeptide CS-1 corresponds to residues 1961–1985.

Another useful polypeptide in the method of the present invention is:

ile-thr-val-tyr-ala-val-thr-gly-arg-gly-asp-ser-pro-ala-ser-ser-lys-pro-ile-ser (MC-2) [sequence No. 6]. This polypeptide corresponds to residues 1485–1504. With the exception of CS-1, all other peptides are common to all isoforms of fibronectin.

Preferred embodiments of the present invention employ multivalent polypeptide and carrier compound conjugates. For example, conjugates having at least 3 and preferably 4 to 8 polypeptide fragments covalently bound to a carrier compound such as ovalbumin (OA), human serum albumin (HSA), other proteins, and polyethylene glycol (PEG), are useful in the present invention.

According to the present invention, a polypeptide or mixture of polypeptides corresponding to an isolated region of fibronectin residues is employed to suppress inflammation and tissue destruction.

The described method can be employed to treat acute inflammatory and immunological disorders and is particularly well-suited to treat chronic inflammatory disorders. Since it is expected that further digestion/hydrolysis of polypeptides from the 33 kD carboxyl portion of the A chain of fibronectin will yield fragments of substantially equivalent bioactivity, lower molecular weight polypeptides corresponding to isolated residues of the A chain of fibronectin are considered to be within the scope of the present invention. While the method described herein utilizes fibronectin polypeptides I, II, IV, V, CS-1 and MC-2, it is to be understood that polypeptides having shorter sequences of amino acids, as well as other polypeptides corresponding to regions within the A and/or B chains of fibronectin with functionally active sequences, are within the scope of the invention. For example, polypeptides having sequences of about 4 amino acids or larger with functionally active sequences are within the scope of the invention. An example of one such short fragment polypeptide within the scope of the invention is arg-gly-asp-ser.

DETAILED DESCRIPTION OF THE INVENTION

Structure of Fibronectin

Figure 1:
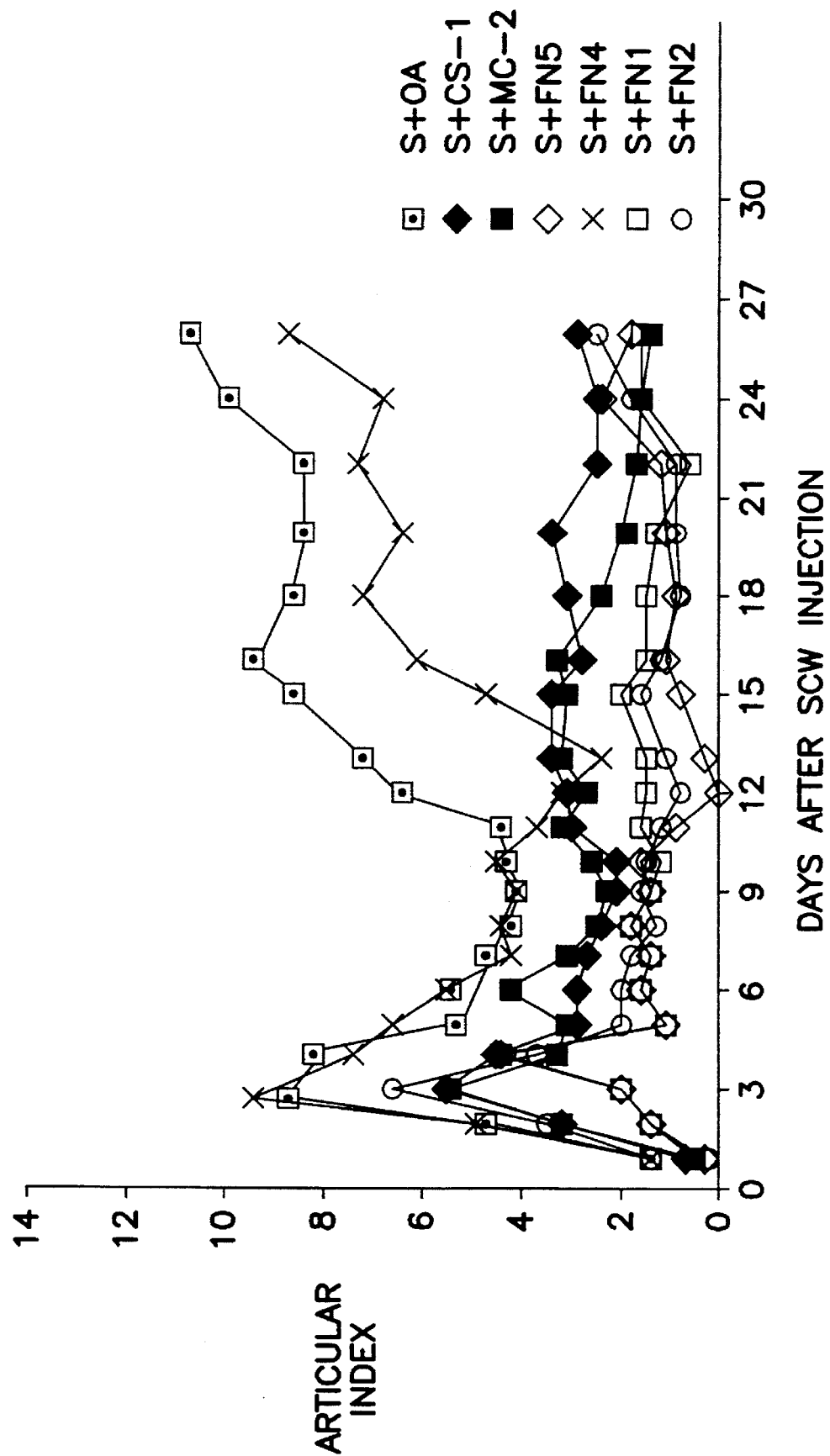
FIG. 1 shows the effect of FN fragments on SCW-induced arthritis. OA-coupled FN fragments were administered i.v. on days 0–4 to SCW-injected rats. Controls included rats given SCW and OA only. Articular indices were determined at indicated intervals (N=3–4/group).

The structure of fibronectin has been previously described in U.S. Pat. Nos. 4,839,464 and 5,019,646, the disclosures of which are incorporated by reference herein. The A chain digest contains a 33 kD fragment (domain V) and a 31 kD fragment (domain VI). The polypeptides useful for the present invention correspond to isolated regions of domain V, which is common to all isoforms of FN.

Synthesis of Polypeptides

Polypeptides employed in the method of the present invention are described in the above-referenced U.S. Pat. Nos. 4,839,464 and 5,019,646.

The significant chemical properties of peptides useful in the present invention are summarized in Table I, below:

TABLE I

| Peptide | | Residue Nos. | Hydropathy Index | Net Charge |
|---|---|---|---|---|
| I | [sequence No. 1] | 1906–1924 | −24.3 | +2 |
| II | [sequence No. 2] | 1946–1963 | −32.5 | +2 |
| CS-1 | [sequence No. 4] | 1961–1985 | −9.9 | −4 |
| IV | [sequence No. 5] | 1784–1792 | −12.2 | +3 |
| V | [sequence No. 3] | 1892–1899 | −10.8 | +2 |
| MC-2 | [sequence No. 6] | 1485–1504 | −0.8 | −1 |

The polypeptides used in the invention were synthesized using the Merrifield solid phase method. This is the method most commonly used for peptide synthesis, and it is extensively described by J. M. Stewart and J. D. Young in *Solid Phase Peptide Synthesis*, Pierce Chemical Company, pub., Rockford, IL (2d ed., 1984), the disclosure of which is incorporated by reference herein. This method of synthesis is understood to be illustrative only and not intended to limit the scope of the present invention in any way.

The Merrifield system of peptide synthesis uses a 1% cross-linked polystyrene resin functionalized with benzyl chloride groups. The halogens, when reacted with the salt of a protected amino acid, will form an ester, linking it covalently to the resin. The benzyloxy-carbonyl (BOC) group is used to protect the free amino group of the amino acid. This protecting group is removed with 25% trifluoroacetic acid (TCA) in dichloromethane (DCM). The newly exposed amino group is converted to the free base by 10% triethylamine (TEA) in DCM. The next BOC-protected amino acid is then coupled to the free amine of the previous amino acid by the use of dicyclohexylcarbodiimide (DCC). Side chain functional groups of the amino acids are protected during synthesis by TFA stable benzyl derivatives. All of these peptides of the present invention were synthesized at the University of Minnesota microchemical facility by the use of a Beckman System 990 peptide synthesizer.

Following synthesis of a blocked polypeptide on the resin, the polypeptide resin is treated with anhydrous hydrofluoric acid (HF) to cleave the benzyl ester linkage to the resin and thus to release the free polypeptide. The benzyl-derived side chain protecting groups are also removed by the HF treatment. The polypeptide is then extracted from the resin, using 1.0M acetic acid, followed by lyophilization of the extract.

Lyophilized crude polypeptides are purified by preparative high performance liquid chromatography (HPLC) by reverse phase technique on a C-18 column. A typical elution gradient is 0% to 60% acetonitrile with 0.1% TFA in $H_2O$. Absorbance of the eluant is monitored at 220 nm, and fractions are collected and lyophilized.

Characterization of the purified polypeptides is by amino acid analysis. The polypeptides are first hydrolyzed anaerobically for 24 hours at 110° C. in 6M HCl (constant boiling) or in 4N methane sulfonic acid, when cysteine or tryptophan are present. The hydrolyzed amino acids are separated by ion exchange chromatography using a Beckman System 6300 amino acid analyzer, using citrate buffers supplied by Beckman. Quantitation is by absorbance at 440 and 570 nm, and comparison with standard curves. The polypeptides may be further characterized by sequence determination. This approach is especially useful for longer polypeptides, where amino acid composition data are inherently less informative. Sequence determination is carried out by sequential Edman degradation from the amino terminus, automated on a Model 470A gas-phase sequenator (Applied Biosystems, Inc.), by the methodology of R. M. Hewick et al., *J. Biol. Chem.*, 256, 7990 (1981).

Polypeptide Carrier Conjugates

Polypeptides synthesized can be employed in the present invention in a monovalent state (i.e., free polypeptide or single polypeptide fragment coupled to a carrier molecule such as a biological carrier, including collagen, a glycosaminoglycan or a proteoglycan, or albumin or the like). Preferably, as described below, to treat chronic inflammatory disorders, conjugates of multiple polypeptide fragments bound to a carrier molecule such as OA, HSA, other proteins, PEG, or the like are employed. Such modifications can increase the apparent affinity or change the circulatory half-life. The number of polypeptide fragments associated with or bound to each carrier molecule can be varied, but from about 4 to about 8 polypeptide fragments per carrier molecule are obtained under these coupling conditions.

Treatment of Inflammatory Disorders

As noted above, the polypeptides and their compositions modulate inflammation and are therefore useful in the treatment of a number of disease states in which aberrant inflammation plays a detrimental role. The method of the present invention is used to treat patients, most particularly humans afflicted with acute or chronic inflammatory disorders involving inflammation, tissue swelling, and/or bone and cartilage degradation. Inflammatory disease refers to a condition in which activation of leukocytes leads to an impairment of normal physiologic function. Examples of such conditions include acute and chronic inflammation, immune and auto-immune disorders such as osteoarthritis, rheumatoid arthritis, IBD (inflammatory bowel disease), sepsis, ARDs (acute respiratory distress syndrome), lupus, MS, graft rejection, cirrhosis, sarcoidosis, granulomatous lesions, periodontitis/gingivitis, and others. Polypeptides corresponding to isolated fibronectin residues can be used to treat inflammatory disorders. Although not necessary to practicing the invention, it is believed that immunosuppressive activity of fibronectin A chain-derived polypeptides block leukocyte adhesion to endothelial cells and/or extracellular matrix, thus affecting leukocyte adhesion and recruitment at sites of inflammation. The method is particularly well suited for treating chronic inflammatory disorders or disease conditions of the type described above.

Patient treatment using the method of the present invention involves administering therapeutic amounts of the polypeptide composition. In the context of the present invention, the terms "treat" and "therapy" and the like refer to alleviate, slow the progression, prophylaxis, attenuation or cure of existing disease. A polypeptide composition may be formulated with conventional pharmaceutically acceptable parenteral vehicles for administration by injection. These vehicles comprise substances which are essentially nontoxic and nontherapeutic such as water, saline, Ringer's solution, dextrose solution, Hank's solution, or the like. It is to be understood that polypeptide formulations may also include small amounts of adjuvants such as buffers and preservatives to maintain isotonicity, physiological and pH stability. Preferably, the polypeptide or polypeptide carrier molecule conjugate is formulated in purified form substantially free of aggregates and other protein at concentrations ranging from about 0.1 to about 10 mg/ml.

As indicated by the above formulation, the polypeptide may be administered parenterally. In the case of some diseases, the polypeptide can be delivered or administered topically, by transdermal patches, intravenously, intraperitoneally, in aerosol form, orally, or in drops, among other methods. When the polypeptide is administered intravenously, it can be delivered as a bolus or on a continuous basis.

The dose of the polypeptide formulation to be administered will depend upon the patient and the patient's medical history, and the severity of the disease process. However, the dose should be sufficient to alleviate inflammation and tissue damage of the patient. Dosages for adult humans envisioned by the present invention and considered to be therapeutically effective will range from between about 10 and 100 mg/kg/day; however, lower and higher amounts could be more appropriate.

The invention will be further described by reference to the following detailed examples.

EXAMPLE

Methods

Reagents

Fibronectin peptides were coupled to ovalbumin (OA; chicken egg, grade III, Sigman, St. Louis, Mo.) by dissolving equal amounts of lyophilized peptides (2–10 mg) and OA in a small volume of water (0.5–2 ml). In a second tube, ten times the amount of peptide of EDC (1-ethyl-3-(3-dimethylaminopropyl)carboiimide hydrochloride was dissolved in water (300 μl). The EDC solution was added to the peptide/OA mixture and rotated at 4 degrees for 2–18 hours. The mixture was then dialyzed into 4 L of PBS (Phosphate Buffered Saline, pH 7.4, NIH Media Unit), changing dialysis several times. Fibronectin polypeptide ovalbumin conjugates prepared contained about 4 to 5 polypeptide fragments per ovalbumin molecule as determined by radiolabelling the peptide fragments prior to coupling and then evaluating the amount bound after coupling.

An additional study was performed in which the FN peptide fragments were resuspended in PBS at a concentration of 2 mg/ml.

Animals.

Specific pathogen-free inbred Lewis (LEW) female rats were obtained from Harlan Sprague Dawley, Inc. (Indianapolis, Ind.). The animals were approximately 100 g at the initiation of the experiments and were housed in ventilator filter units (Lab Products, Maywood, N.J.). All injections were administered with metophane anesthesia. Studies were performed following NIH-approved animal protocol.

Preparation of bacterial cell wall fragments.

Group A streptococci from the American Type Culture Collection (SCW; ATCC 10389) were grown in Todd Hewitt Broth (Difco, Detroit, Mich.), harvested in log phase, washed with PBS, incubated twice at 50° C. with 4% sodium dodecyl sulfate (SDS), washed extensively to remove the SDS, and then incubated sequentially with DNase, RNase, and trypsin (4 hr at 37° C. each; Sigma). The washed cell walls were then sonicated for 70 minutes and the cell wall fragments remaining in the supernatant after 0.5 hr of centrifugation at 10,000 g were utilized for injection. The total amount of rhamnose in the cell wall-containing supernatant was determined by the Dische-Shettles method, Dische and Shettles, *J. Bio. Chem.*, 175, 595–603 (1948).

Induction, monitoring and treatment of arthritis.

On day 0, each rat was injected intraperitoneally (i.p.) with an aqueous suspension of cell wall fragments containing 2.5 mg of rhamnose. In addition, each rat was injected intravenously (i.v.) with 1 mg of the coupled peptides in 0.5 ml PBS daily for five days. Control animals received an equal volume of PBS or OA. The rats were checked daily during the acute response and every other day thereafter. The severity of the arthritis manifested by each rat was determined using a "joint count" (Articular Index; AI). This score is derived by the summation of a score of 0 (normal) to 4 (maximum) for each extremity based on the degree of swelling, erythema, and distortion (maximum total score of 16). Additional studies examined the therapeutic efficacy of the peptides by administration on days 11–15, after the acute response had subsided, and at the initiation of the chronic phase.

In a parallel study, the efficacy of uncoupled FN peptides by i.v. administration in 0.5 ml PBS (1 mg) on days 0–4 was investigated.

Histologic Evaluation.

All animals were examined by routine histologic techniques. Joints were either fixed in 10% formalin, decalcified, sectioned, and stained with hematoxylin and eosin or quick-frozen in O.C.T. compound (Miles Scientific, Naperville, Ill.) by immersion in a mixture of dry ice and acetone, and sectioned for additional staining.

Results

Effect of FN fragments on the development of SCW-induced arthritis.

Daily i.v. administration of OA-coupled FN peptides on days 0–4 had an inhibitory effect on the evolution of arthritic lesions. The acute, neutrophil-mediated phase was blunted, but more dramatical was the suppression of the chronic, destructive phase (FIG. 1). On day 3, at the height of the acute response, the articular index (AI) was 8.5±1.2 for the OA-treated, SCW-injected rats, which was reduced with treatment to 5.6±0.8 with CS-1, 5.5±0.84 with MC-2, 5.7±1.1 with FNV, 6.6±1.9 with FNII, and 2.0±0.9 with FNI. Under these conditions, treatment with FNIV did not suppress the acute response, with an AI of 9.2±0.97.

By day 27, when chronic inflammation is well established, the differences were even more pronounced. The AI of the OA-treated, SCW-injected rats was 10.5±0.3. FNIV was the least effective in suppressing arthritis (AI=8.6±0.3). However, the other coupled peptides suppressed the AI to 2.5±0.7 for CS-1, 1.25±0.25 for MC-2, 1.7± 0.5 for FNV, 2.3±0.9 for FNII and 1.5±1.1 for FNI. No evidence of toxicity based on weight loss or hematocrit levels was observed in the peptide-treated groups.

Effect of FN fragments on the evolution of chronic arthritic lesions.

Figure 2:
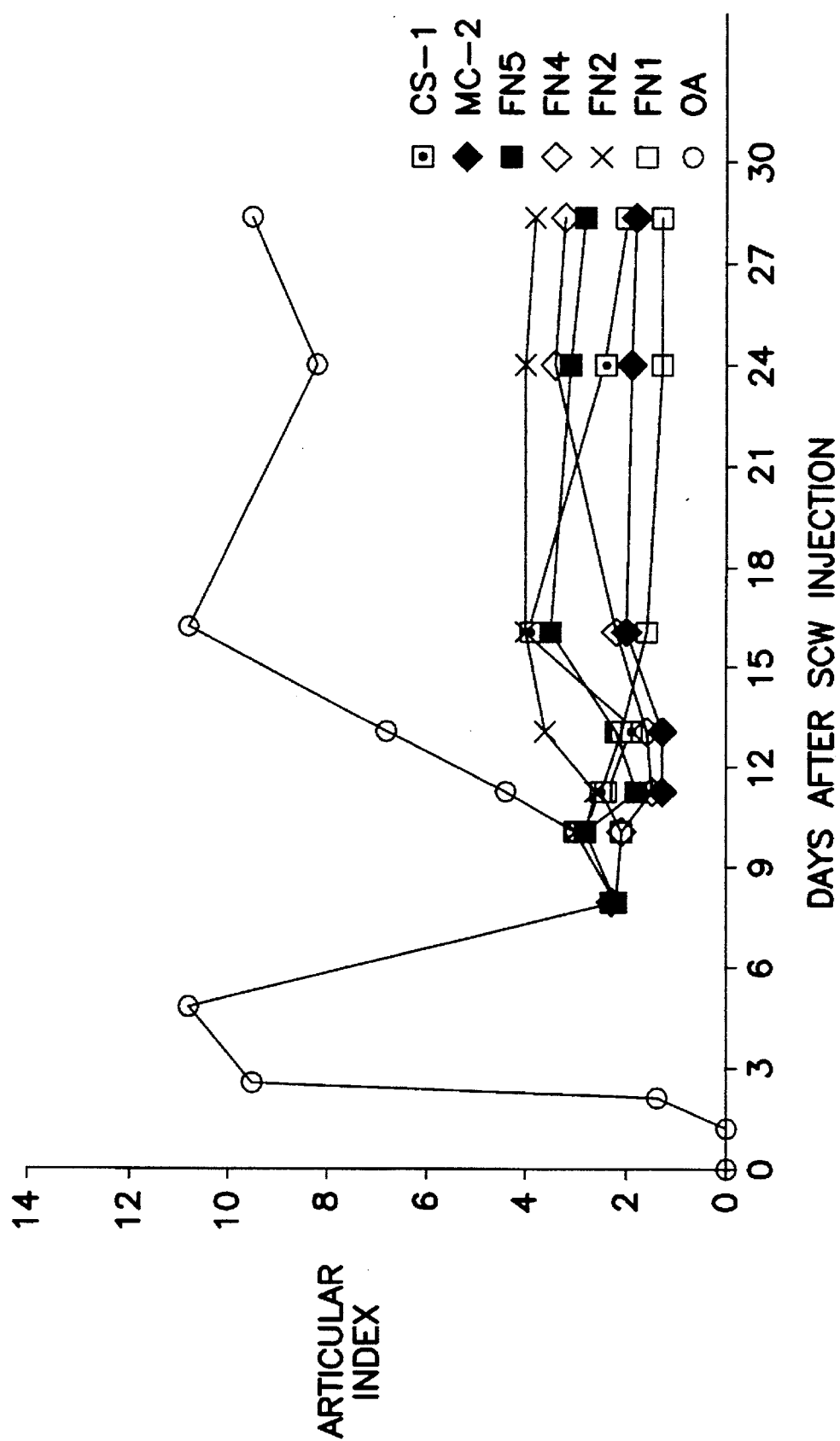
FIG. 2 shows the effect of FN fragments on chronic synovitis. OA-coupled FN fragments were administered i.v. on days 11–15 to SCW-injected rats. Control SCW-injected rats received OA. Articular indices were determined at indicated intervals (N=3–4/group).

To determine if the peptides could therapeutically suppress the chronic synovitis, administration was initiated after the acute response. All the animals were randomized so that the AI for each group was similar, and peptide administration was started on day 11 and continued daily until day 15 (5 days), well into the chronic phase. Surprisingly, all the FN peptides were suppressive (FIG. 2). On day 28, the OA-treated SCW-injected group had an AI of 11.3±0.5. Treatment with CS-1 reduced the AI to 4.2±1.5, MC-2 reduced it to 2.7±1.9, FNV to 4.5±1.0, FNIV to 2.0±1.0, FNII to 4.9±1.2, and FNI to 1.5±1.0. Based on these data, the primary target at this stage appears to be of leukocyte lineage (lymphocytes and/or macrophages) which are the central mediators of the chronic cell-mediated phase of arthritis in this model [Malone et al., *J. Clin. Invest.*, 76: 1042–1056 (1985); and Wahl et al., *J. Exp. Med.*, 168: 1403–1417 (1988)].

Effect of uncoupled FN fragments on the development of SCW-induced arthritis.

Figure 3:
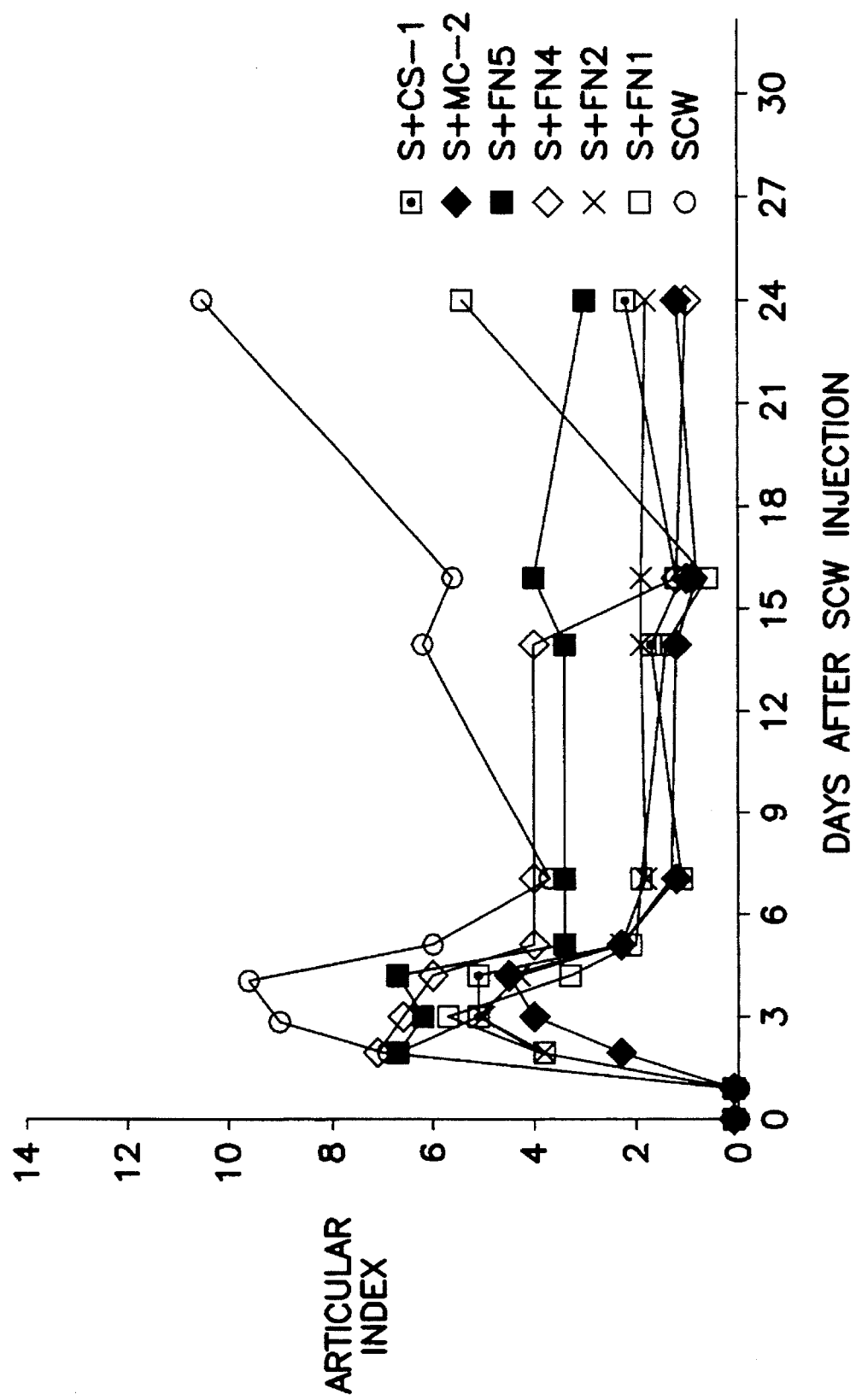
FIG. 3 shows the effect of uncoupled FN fragments on SCW-induced arthritis. FN fragments were administered i.v. on days 0–4 to SCW-injected rats. Controls included rats injected with SCW only. Articular indices were determined at indicated intervals (n=1–3/group).

Daily i.v. administration of uncoupled FN peptides on days 0–4 suggested an inhibitory effect on the development and maintenance of arthritis. In initial studies, the acute phase was slightly suppressed by all fragments (FIG. 3). On day 4, at the peak of the acute response, the AI of the untreated rats was 9.5, compared to a range of 3.3 to 6.7 after treatment with the FN fragments. Furthermore, the effect was sustained until day 24 when the AI of the untreated arthritic rats was 9.7, compared to 2.2 for the CS-1 treated animals, 1.3 after MC-2 treatment, 2.8 after FNV treatment, 1.0 after FNIV treatment, 1.7 after FNII treatment, and 5.0 after FNI treatment. These data show that the uncoupled FN fragments, in addition to multivalent FN peptides coupled to carriers or polymers (e.g., OA), are effective in suppressing SCW-induced arthritis.

Effect of FN fragments on the histopathogenesis of SCW-induced arthritis.

SCW induces synovial cell lining hyperplasia with villus formation, mononuclear cell infiltration, synovial proliferation, bone erosion, and ultimately, joint destruction which follows a pattern similar to human arthritis. Following peptide administration from days 0 to 4, the joints exhibited markedly reduced histopathology when evaluated at the termination of the experiment. There was less infiltration of inflammatory cells, less synovial hyperplasia, and little evidence of erosions. In contrast, the OA-treated, SCW-injected rats exhibited the destructive joint abnormalities characteristic of untreated groups of animals. Administration of the peptides during the early chronic phase of disease also effectively reduced the chronic, destructive pathology.

Based on the above example and written description, it has been shown that selected peptides derived from the extracellular matrix protein, fibronectin, are effective inhibitors of acute and chronic inflammatory pathology. Administration of fibronectin peptides with specific binding properties for integrins and cell surface proteoglycans (PG) or other CAMs can suppress joint diseases such as rheumatoid arthritis, acute or chronic inflammatory disorders, and others.

The invention has been described with reference to various specific and preferred embodiments and techniques. It should be understood that many variations and modifications may be made while remaining within the spirit and scope of the invention.

---

What is claimed is:

1. A method for treating arthritis in a mammal comprising: administering to said mammal to suppress inflammation an effective amount of a composition which includes a polypeptide corresponding to an amino acid sequence within the 33 kD carboxyl terminal, heparin-binding region located on the A chain of fibronectin, wherein the polypeptide has a formula selected from the group consisting of tyr-glu-lys-pro-gly-ser-pro-pro-arg-glu-val-val-pro-arg-pro-arg-pro-gly-val, lys-asn-asn-gln-lys-ser-glu-pro-leu-ile-gly-arg-lys-lys-thr, trp-gln-pro-pro-arg-ala-arg-ile, asp-glu-leu-pro-gln-leu-val-thr-leu-pro-his-pro-asn-leu-his-gly-pro-glu-ile-leu-asp-val-pro-ser-thr, and ser-pro-pro-arg-arg-ala-arg-val-thr.

2. The method of claim 1 wherein said mammal is a human.

3. The method of claim 1 wherein said composition includes a polypeptide having the formula: tyr-glu-lys-pro-gly-ser-pro-pro-arg-glu-val-val-pro-arg-pro-arg-pro-gly-val.

4. The method of claim 1 wherein said composition includes a polypeptide having the formula: lys-asn-asn-gln-lys-ser-glu-pro-leu-ile-gly-arg-lys-lys-thr.

5. The method of claim 1 wherein said composition includes a polypeptide having the formula: trp-gln-pro-pro-arg-ala-arg-ile.

6. The method of claim 1 wherein said composition includes a polypeptide having the formula: asp-glu-leu-pro-gln-leu-val-thr-leu-pro-his-pro-asn-leu-his-gly-pro-glu-ile-leu-asp-val-pro-ser-thr.

7. The method of claim 1 wherein said composition includes a polypeptide having the formula: ser-pro-pro-arg-arg-ala-arg-val-thr.

8. The method of claim 1 wherein said polypeptide is administered as a conjugate having from three to eight of the polypeptides bound to a carrier molecule.

9. The method of claim 8 wherein said carrier is ovalbumin.

10. A method for treating arthritis in a mammal comprising: administering to said mammal to suppress inflammation an effective amount of a polypeptide and biological carrier molecule conjugate having three or more of the following polypeptides bound to each carrier molecule of said conjugate having the formula: tyr-glu-lys-pro-gly-ser-pro-pro-arg-glu-val-val-pro-arg-pro-arg-pro-gly-val, lys-asn-asn-gln-lys-ser-glu-pro-leu-ile-gly-arg-lys-lys-thr, trp-gln-pro-pro-arg-ala-arg-ile, asp-glu-leu-pro-gln-leu-val-thr-leu-pro-his-pro-asn-leu-his-gly-pro-glu-ile-leu-asp-val-pro-ser-thr, ser-pro-pro-arg-arg-ala-arg-val-thr.

11. The method of claim 10 wherein said mammal is a human.

12. A method for treating arthritis in a patient comprising: administering to said patient to suppress inflammation an effective amount of a polypeptide of the formula: tyr-gly-lys-pro-gly-ser-pro-pro-arg-glu-val-val-pro-arg-pro-arg-pro-gly-val.

13. The method of claim 12 wherein said polypeptide is administered as a conjugate having from three to eight of the polypeptides bound to a carrier molecule.

14. A method for treating arthritis in a patient comprising: administering to said patient to suppress inflammation an effective amount of a polypeptide of the formula: lys-asn-asn-gln-lys-ser-glu-pro-leu-ile-gly-arg-lys-lys-thr.

15. A method for treating arthritis in a patient comprising: administering to said patient to suppress inflammation an effective amount of a polypeptide of the formula: trp-gln-pro-pro-arg-ala-arg-ile.

16. A method for treating arthritis in a patient comprising: administering to said patient to suppress inflammation an effective amount of a polypeptide of the formula: ile-thr-val-tyr-ala-val-thr-gly-arg-gly-asp-ser-pro-ala-ser-ser-lys-pro-ile-ser.

17. The method of claim 15 wherein said polypeptide is administered as a conjugate having from three to eight of the polypeptides bound to a biological carrier molecule.

* * * * *

UNITED STATES PATENT AND TRADEMARK OFFICE
CERTIFICATE OF CORRECTION

PATENT NO. : 5,591,719

DATED : January 7, 1997

INVENTOR(S) : Leo T. Furcht, et al.

It is certified that error appears in the above-identified patent and that said Letters Patent is hereby corrected as shown below:

Column 1,
Before the "BACKGROUND OF THE INVENTION" insert as follows:

--GOVERNMENT SUPPORT--

--The present invention was made with the support of Grant Nos. CA 43924 and CA 21463 from the National Institutes of Health. The government has certain rights in the invention including those under the grants noted above.--

Signed and Sealed this

Seventh Day of October, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 19 amino acid residues
        ( B ) TYPE: Amino Acid
        ( D ) TOPOLOGY: Linear ( i i ) MOLECULE TYPE: Peptide ( v ) FRAGMENT TYPE: Internal Fragment ( v i ) ORIGINAL SOURCE: Synthetically Derived ( i x ) FEATURE:
        ( A ) NAME/KEY: Fragment of the 33 kD carboxy
           terminal heparin-binding fragment of the A
           chain of fibronectin
        ( B ) LOCATION: Represents isolated fibronectin
           residues 1906-1924 from all plasma isoforms
           of fibronectin ( x i ) SEQUENCE DESCRIPTION: SEQ ID NO:1:

Tyr Glu Lys Pro Gly Ser Pro Pro Arg Glu Val Val Pro Arg Pro Arg
1               5                   10                  15
    Pro Gly Val ( 2 ) INFORMATION FOR SEQ ID NO:2:

( i ) SEQUENCE CHARACTERISTICS:
  ( A ) LENGTH: 15 amino acid residues
  ( B ) TYPE: Amino Acid
  ( D ) TOPOLOGY: Linear ( i i ) MOLECULE TYPE: Peptide ( v ) FRAGMENT TYPE: Internal Fragment ( v i ) ORIGINAL SOURCE: Synthetically Derived ( i x ) FEATURE:
  ( A ) NAME/KEY: Fragment of the 33 kD carboxy
    terminal heparin-binding fragment of the A
    chain of fibronectin
  ( B ) LOCATION: Represents isolated fibronectin
    residues 1946-1961 from all plasma isoforms
    of fibronectin ( x i ) SEQUENCE DESCRIPTION: SEQ ID NO:2:

```
Lys Asn Asn Gln Lys Ser Glu Pro Leu Ile Gly Arg Lys Lys Thr
1               5                   10                  15
```

( 2 ) INFORMATION FOR SEQ ID NO:3:

( i ) SEQUENCE CHARACTERISTICS:
    ( A ) LENGTH: 8 amino acid residues
    ( B ) TYPE: Amino Acid
    ( D ) TOPOLOGY: Linear ( i i ) MOLECULE TYPE: Peptide ( v ) FRAGMENT TYPE: Internal Fragment ( v i ) ORIGINAL SOURCE: Synthetically Derived ( i x ) FEATURE:
    ( A ) NAME/KEY: Fragment of the 33 kD carboxy
      terminal heparin-binding fragment of the A
      chain of fibronectin
    ( B ) LOCATION: Represents isolated fibronectin
      residues 1892-1899 from all plasma isoforms
      of fibronectin ( x i ) SEQUENCE DESCRIPTION: SEQ ID NO:3:

```
Trp Gln Pro Pro Arg Ala Arg Ile
1               5
```

( 2 ) INFORMATION FOR SEQ ID NO:4:

( i ) SEQUENCE CHARACTERISTICS:
    ( A ) LENGTH: 25 amino acid residues
    ( B ) TYPE: Amino Acid
    ( D ) TOPOLOGY: Linear ( i i ) MOLECULE TYPE: Peptide ( v ) FRAGMENT TYPE: Internal Fragment ( v i ) ORIGINAL SOURCE: Synthetically Derived ( i x ) FEATURE:
    ( A ) NAME/KEY: Fragment of the 33 kD carboxy
      terminal heparin-binding fragment of the A
      chain of fibronectin
    ( B ) LOCATION: Represents isolated fibronectin
      residues 1961-1985 from the A chain of human
      plasma fibronectin ( x i ) SEQUENCE DESCRIPTION: SEQ ID NO:4:

```
Asp Glu Leu Pro Gln Leu Val Thr Leu Pro His Pro Asn Leu His Gly
1               5                   10                  15

Pro Glu Ile Leu Asp Val Pro Ser Thr
```

(2) INFORMATION FOR SEQ ID NO:5:

(i) SEQUENCE CHARACTERISTICS:
        (A) LENGTH: 9 amino acid residues
        (B) TYPE: Amino Acid
        (D) TOPOLOGY: Linear (ii) MOLECULE TYPE: Peptide (v) FRAGMENT TYPE: Internal Fragment (vi) ORIGINAL SOURCE: Synthetically Derived (ix) FEATURE:
        (A) NAME/KEY: Fragment of the 33 kD carboxy
            terminal heparin-binding fragment of the A
            chain of fibronectin
        (B) LOCATION: Represents isolated fibronectin
            residues 1784-1792 from all plasma isoforms
            of fibronectin (xi) SEQUENCE DESCRIPTION: SEQ ID NO:5:

Ser Pro Pro Arg Arg Ala Arg Val Thr
1               5

(2) INFORMATION FOR SEQ ID NO:6:

(i) SEQUENCE CHARACTERISTICS:
        (A) LENGTH: 20 amino acid residues
        (B) TYPE: Amino Acid
        (D) TOPOLOGY: Linear (ii) MOLECULE TYPE: Peptide (v) FRAGMENT TYPE: Internal Fragment (vi) ORIGINAL SOURCE: Synthetically Derived (ix) FEATURE:
        (A) NAME/KEY: 75 kD tryptic fragment of
            fibronectin that promotes cell adhesion
        (B) LOCATION: Represents isolated fibronectin
            residues 1485-1504 from all plasma isoforms
            of fibronectin (xi) SEQUENCE DESCRIPTION: SEQ ID NO:6:

Ile Thr Val Tyr Ala Val Thr Gly Arg Gly Asp Ser Pro Ala Ser Ser
1            5                  10                 15

Lys Pro Ile Ser
         20